United States Patent [19]

Kramer et al.

[11] Patent Number: 4,908,350

[45] Date of Patent: Mar. 13, 1990

[54] HYPEROSMOTIC/HYPERONCOTIC SOLUTIONS FOR RESUSCITATION OF HYPODYNAMIC SHOCK

[75] Inventors: George C. Kramer, Davis; James W. Holcroft, El Macero, both of Calif.

[73] Assignee: The Regents of the University of California, Berkeley, Calif.

[21] Appl. No.: 163,137

[22] Filed: Feb. 24, 1988

Related U.S. Application Data

[63] Continuation of Ser. No. 793,573, Oct. 31, 1985, abandoned.

[51] Int. Cl.$^4$ ............... A61K 37/02; A61K 33/14; A61K 31/70
[52] U.S. Cl. ........................... 514/2; 514/23; 514/59; 514/60; 514/921; 424/680
[58] Field of Search ............ 514/2, 59, 921, 60, 514/23; 424/101, 153, 680

[56] References Cited

U.S. PATENT DOCUMENTS

| | | | |
|---|---|---|---|
| 3,864,478 | 2/1975 | Bonhard | 424/101 |
| 3,993,750 | 11/1976 | Fox, Jr. | 424/128 |
| 4,049,795 | 9/1977 | Laborit | 514/23 |
| 4,271,144 | 6/1981 | Holly | 424/78 |
| 4,308,255 | 12/1981 | Raj et al. | 424/153 |

OTHER PUBLICATIONS

Modig, Biol. Abstracts 78(3): 21473 No. 2745 1983.
Pristoupil, Chem. Abstracts vol. 82, 1975, No. 47728b.
Hyperosmotic NaCl and Severe Hemorrhagic Shock by I. T. Velasco, V. Pontieri, M. Rocha E. Silva, Jr. and O. U. Lopes, pp. H664–673 1980 (Heart Circ. Physiol. 8).
Hyperosmotic NaCl and Severe Hemorrhagic Shock: Role of the Innervated Lung, O. U. Lopes, V. Pontieri, M. Rocha E. Silva, Jr., and I. T. Velasco (Am. J. Physiol 241) (Heart Circ. Physiol. 20: H883–H890) 1981.
Body Fluid Changes During Hypertonic Lactated Saline Solution Therapy for Burn Shock, Shuji Shimazaki, M.D. et al., The Journal of Trauma, vol. 17, pp. 38–43 (1977).
Treatment of Experimental Shock; Comparison of the Effects of Non-epinephrine, Dibenzyline, Dextran, Whole Blood, and Balanced Saline Solutions, R. F. Rush, Jr., M.D., Surgery vol. 61, No. 6, pp. 938–944 (1967).
Comparison of Isotonic and Hypertonic Solutions and Blood Flow and Oxygen Consumption in the Initial Treatment of Hemorrhagic Shock, Arthur E. Baue, M.D. et al., J. of Trauma, vol. 7, No. 5, pp. 743–756 (1967).
Lopes et al., Chemical Abstracts vol. 96:617p (1982).
Velasco et al., Chemical Abstracts vol. 93:215562r (1980).
Silbert, Samuel. The treatment of thromboangiitis obliterans. Journal A.M.A. 1759–1761 (Jun. 5, 1926).
Fraser, John; Cowell, E. M. Clinical Study of Blood Pressure in Wound Conditions. Journal A.M.A. Feb. 23, 1918.
Danowski, T. S.; Winkler, A. W.; Elkinton, J. T. The Treatment of Shock Due to Salt Depletion; Comparison of the Hemodynamic Effects of Isotonic Saline, of Hypertonic Saline, and of Isotonic Glucose Solutions. J.C.I. 215:130–138 (1946).
Rush, R. F. Jr. Treatment of Experimental Shock: Comparison of the Effects of Nonepinephrine, Dibenzyline, Dextran, Whole Blood, and Balance Saline Solutions. Surgery, vol. 61, No. 6, 938–944. 1967.
Brooks, D. K.; Williams; W. G.; Morley, R. W.; Whiteman, R. Osmolar and Electrolyte Changes in Haemorrhagic Shock. The Lancet. pp. 521,527, Mar. 9, 1963.

*Primary Examiner*—Jacqueline M. Stone
*Attorney, Agent, or Firm*—Pretty, Schroeder, Brueggemann & Clark

[57] ABSTRACT

A physiologically acceptable solution which is both hyperosmotic and hyperoncotic with respect to blood plasma and has utility in treating patients experiencing or threatening to experience hypodynamic shock. The physiologically acceptable solution comprises a hyperosmotic concentration of a crystalloid (in excess of about 1800 mOsms) and hyperoncotic concentration of a colloid (in excess of about 30 mm Hg). The physiologically acceptable solution is easily administered by single, rapid infusion of approximately 4 to 5 ml/kg of body weight and results in a rapid and sustained normalization of circulatory function.

20 Claims, 1 Drawing Sheet

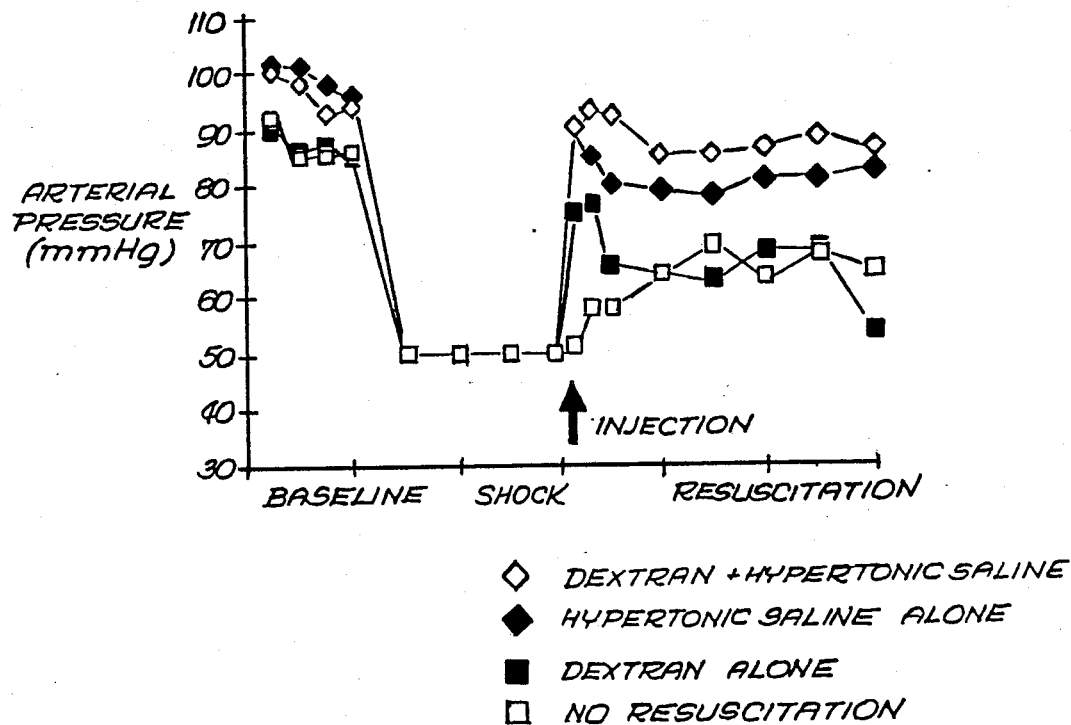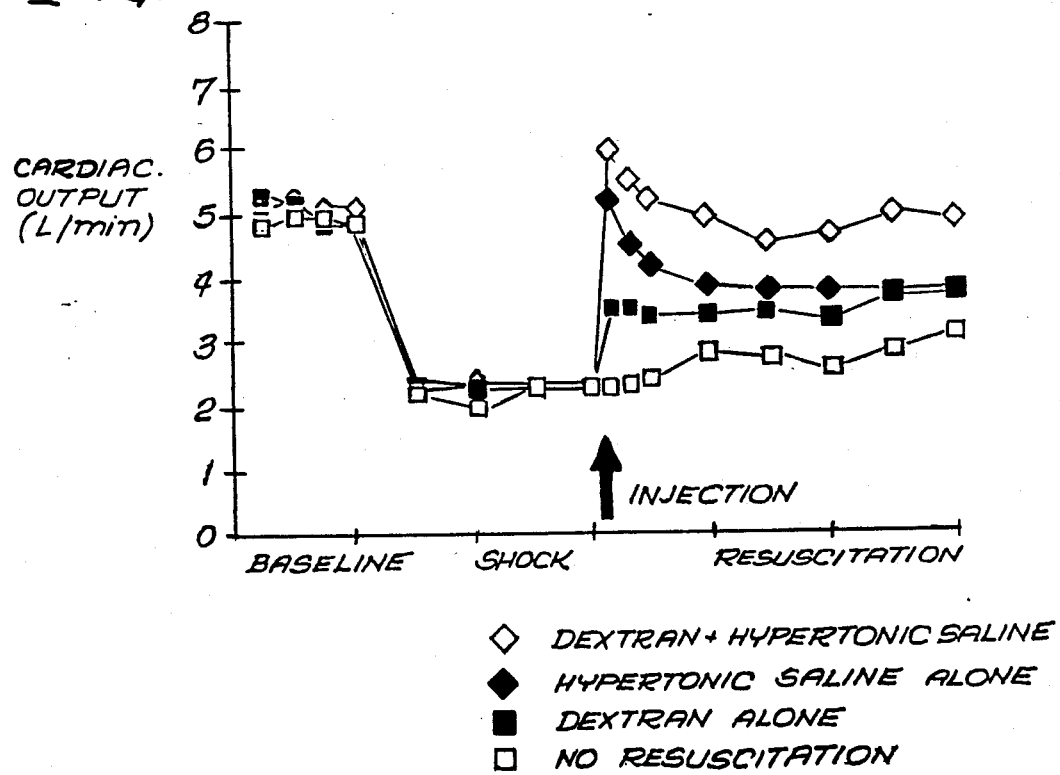

HYPEROSMOTIC/HYPERONCOTIC SOLUTIONS FOR RESUSCITATION OF HYPODYNAMIC SHOCK

This invention was made with Government support under Grant No.: DAMD 17-83-C-3175 with the United States Department of Defense and the University of California. The Government has certain rights in this invention.

This is a continuation of application Ser. No. 793,573, filed Oct. 31, 1985, which was abandoned upon the filing hereof.

This invention relates generally to the area of treatments for circulatory shock and more specifically to a solution which is both hyperosmotic and hyperoncotic for use in preventing and treating hypodynamic shock.

Trauma is the major cause of death in persons under 38 years of age and accounts for over 150,000 deaths per year in this country. Among the most hazardous consequences of traumatic injury is bleeding. The loss of more than 50% of the starting blood volume is not unusual in such injuries and is fatal if not treated promptly.

While field therapy of many medical emergencies, such as cardiac arrest, asthmatic attacks and diabetic crises has become increasingly successful due to the ever increasing armanentarium of effective drugs, considerably less success has been realized with field treatment of trauma and shock. No drugs have proven effective for the initial treatment of trauma victims. Initial therapy of trauma and hemorrhage currently centers n effecting the cessation of bleeding and on the infusion of large volumes of solutions to replace lost blood volume. Large volume infusion (2 to 8 liters) has generally been considered necessary to restore normal circulatory functions such as arterial blood pressure, cardiac output, oxygen consumption and renal function. Such treatment must be accomplished rapidly to be effective.

The infusion of large volumes of solution involves risks and complications, however. Fluid overload, or "overexpansion", and congestive pulmonary atelectasis may result after use of excessive amounts of fluid. Limited personnel and difficult conditions at the site of an accident make adequate field resuscitation difficult to impossible. In addition to the time necessary merely to infuse such volumes, critical minutes are lost due to difficulties in gaining access to the vascular system. Paramedical personnel must be highly trained to perform such operations. As a result, the average trauma patient has received only 700 ml of fluid prior to arrival in the emergency room, a volume which is normally insufficient to effectively treat hypodynamic shock.

Fluid replacement infusion normally utilizes solutions which have a similar osmolarity to blood plasma. Osmolarity refers to the total concentration of molecules or solutes in a solution. Water will tend to move across a semi-permeable membrane into a solution having a higher concentration of solutes. Thus, the introduction into, for example, the blood vessels, of a fluid having an osmolarity higher than that of normal body fluids will establish an osmotic gradient across the membranes, resulting in an initial change of fluid volume within the vascular system. Osmolarity is generally expressed as millimoles per liter of solution or mOsms.

Small molecules will themselves gradually leak out of the blood vessels, however, so that vascular volume will return eventually to preinfusion levels. Larger molecules, such as colloids, will not escape from the blood vessels as easily, and thus will maintain an osmotic gradient across the membranes. Because the osmotic pressure exerted by colloids in the blood, which is in the range of about 1 to 2 mOsms, is so much smaller than that of the total osmotic pressure generated by all solutes, colloidal osmotic pressure, or oncotic pressure, is expressed in terms of mm Hg. Blood plasma has an osmolarity of about 283 to 295 mOsms and an oncotic pressure of about 25 mm Hg. Solutions which exceed these levels are termed hyperosmotic or hyperoncotic, respectively.

Recently, attempts have been made to treat animals in hypodynamic shock with highly hyperosmotic saline solutions, having an osmolarity in the range of 2400 mOsms. Such treatment has the advantage of requiring smaller total fluid volume and results in brief initial promotion of circulatory function. Because this improvement is short-lived, however, with critical parameters deteriorating over time, hyperosmotic saline does not provide an effective, sustained treatment for shock.

There thus exists a longfelt need for an effective solution for treating shock victims, particularly those experiencing hypodynamic shock. Administration of a small volume of such a solution should result in the rapid and sustained normalization of circulatory function. Additionally, the solution should be inexpensive and have a long shelf life. The present invention satisfies these needs and provides related advantages as well.

SUMMARY OF THE INVENTION

The present invention provides a physiologically acceptable solution which is both hyperosmotic and hyperoncotic with respect to blood plasma and has utility in treating patients experiencing or threatening to experience hypodynamic shock. When given a small volume of the solution, on the order of 4 to 5 ml/kg of body weight, patients who have lost a significant proportion of their blood volume exhibit immediate, unexpectedly improved and sustained circulatory functioning as indicated by increased arterial pressure, cardiac output, and oxygen consumption and lowered peripheral resistance. Moreover, cellular membrane potentials and intracellular electrolyte balances are thereby restored. In addition, blood flow to the kidneys and other vital organs may be augmented and urine output is unexpectedly and rapidly increased, thereby decreasing the possibility of acute renal failure, a major complication of shock.

In one embodiment, the physiologically acceptable solution comprises a hyperosmotic concentration of a crystalloid (in excess of about 1800 mOsms, preferably about 2000 to 2800 mOsms) and a hyperoncotic concentration of a colloid (in excess of about 30 mm Hg, preferably about 70 mm Hg). This physiologically acceptable solution is inexpensive to manufacture and is not adversely affected by temperature extremes, including freezing. As another aspect of the invention, the physiologically acceptable solution is easily administered by single, rapid infusion of approximately 4 to 5 ml/kg of body weight and results in a rapid and sustained normalization of circulatory function.

Other features and advantages of the present invention will become apparent from the following, more detailed description which illustrates, by way of example, the principles of the invention

BRIEF DESCRIPTION OF THE DRAWINGS

FIG. 1 shows arterial pressure as a function of time in animals receiving a hyperosmotic sodium chloride/hyperoncotic dextran solution and those receiving control solutions.

FIG. 2 shows cardiac output as a function of time in animals receiving a hyperosmotic sodium chloride/hyperoncotic dextran solution and those receiving control solutions.

DETAILED DESCRIPTION OF THE PREFERRED EMBODIMENT

The present invention provides a physiologically acceptable solution which is hyperosmotic and hyperoncotic with respect to blood plasma. The term "physiologically acceptable" as used herein means that a small volume of the solution can be injected directly into a mammal without inducing pathological changes, such as an immune response or metabolic alterations due to toxicity. The physiologically acceptable solution has particular utility for use in preventing or treating hypodynamic shock, and results in an unexpected improvement in circulatory function which is sustained for at least several hours. The solution is effective when administered in small quantities, permitting relatively easy transport and rapid administration, thereby facilitating easy and effective treatment at or near the site of injury.

The solution comprises a crystalloid and a colloid, both of which are present in concentrations exceeding those of human blood plasma, thus establishing an osmotic gradient across the walls of the blood vessels. The crystalloid may be any small molecule which will exert osmotic pressure including, but not limited to, sugars, sugar alcohols, salts, and other ions having molecular weights less than about 1000. Preferably, the crystalloid is sodium chloride, which in water comprises a saline solution. The concentration of the crystalloid is selected to provide an osmolarity which is sufficiently high so as to be effective in restoring circulatory function, without exerting detrimental effect on the cells and tissues or causing adverse physiological effects such as convulsions. Preferably, the osmolarity is between about 1800 to about 3000 mOsms, e.g., 2000 to 2800 mOsms, and ideally about 2400 mOsms.

A colloid is also provided in the solution, selected from physiologically acceptable colloids (i.e., so called plasma volume expanders) having an average molecular weight higher than about 30,000 and usually lower than 400,000, preferably lower than 250,000, for example lower than 100,000. Such colloids include, but are not limited to, dextran, hydroxyethyl starches and gelatins of various average molecular weights and proteins, such as plasma proteins and hemoglobin. Preferably, the colloid is dextran 70 (molecular weight of about 70,000) or dextran 60 (molecular weight of about 60,000). The concentration is selected so as to provide maximum salutory effect without damage to cells or tissues, and the colloidal osmotic pressure is higher than 30 mm Hg, preferably about 70 mm Hg or in excess thereof. Because of the problems of maximum solubility and increasing viscosity which interferes with ease of administration by the means disclosed, the concentration is preferably below about 30% weight/volume.

A hyperosmotic/hyperoncotic solution is advantageously utilized to treat hypodynamic circulatory shock resulting from such cases as hemorrhage, trauma, burns, or shock. It is also useful to treat acute renal failure and cerebral edema. The solution is administered in the field or may be used as an initial treatment in an emergency room or critical care unit where a patient exhibits rapid blood loss or unresponsive hypodynamic circulation. The solution may be infused rapidly in a single bolus through a vascular catheter or may be injected directly into a peripheral vessel, with a concomitant saving of critical time. The solution is effective in unexpectedly low dosages, about 4 to 5 ml/kg of body weight, which amounts to only about 1/10 to 1/80 the volume presently used to treat victims exhibiting shock through conventional volume replacement therapy. Because only such small volumes are necessary, logistical problems of providing the solution at the site of injury are obviated. The same volume of fluid necessary to treat one patient through conventional therapy may be effectively used to treat many patients when a hyperosmotic/hyperoncotic solution is utilized.

After administration of a small volume of a hyperosmotic/hyperoncotic solution, various indicators of circulatory function are found to rapidly achieve normality, and to sustain such normality. Among these indicators are arterial pressure, cardiac output, oxygen consumption, peripheral resistance, urine output, cellular membrane potentials and intracellular electrolyte balance.

EXAMPLE I

COMPARATIVE TREATMENT OF HYPODYNAMIC CIRCULATORY SHOCK IN SHEEP

Solutions of varying composition were used to treat hypodynamic circulatory shock in adult sheep weighing 40 to 50 kg. Chronic cannulation of the thoracic aorta, superior vena cava and pulmonary artery were performed on sheep anesthetized with halothane/nitrous oxide, and silastic and Swan-Ganz thermodilution catheters (Edwards Laboratories, Santa Ana, Calif.) inserted. A Foley catheter was emplaced to monitor urine output. Food and water were withheld for 24 to 36 hours before the beginning of the experimental protocol. Experiments were performed at least 72 hours after surgery.

All experiments were conducted on unanesthetized animals kept unrestrained in cages. Physiological parameters measured and recorded during experiments included vascular pressures (arterial, central venous, pulmonary artery and pulmonary wedge), cardiac output, urine flow rate, heart rate and respiratory rate. Blood samples were taken for subsequent analysis of hematocrit, serum osmolarity and serum $Na^+$, $K^+$ and $Cl^{31}$. After an initial one hour period of baseline data collecting, the sheep were bled to a mean arterial pressure of 50 mm Hg, and maintained at 40 to 55 mm Hg by continued bleeding for the next two hours. Measurement protocols followed those detailed in Example II.

Each experimental sheep received a bolus infusion of about 4 ml/kg of hyperosmotic/hyperoncotic solution (1.2M sodium chloride, 6% weight/volume dextran 70 (Macrodex ®, Pharmacia Fine Chemicals, Piscataway, NJ) in deionized, sterile water; osmolarity≃2400 mOsms, oncotic pressure≃70 mm Hg) and was monitored for three hours. Control sheep were given either no resuscitation, a hyperosmotic sodium chloride solution (1.2M, 2400 mOsms), or a hyperoncotic dextran solution (6% weight/volume, 70 mm Hg). As indicated in FIGS. 1 and 2, administration of all solutions resulted in an enhancement of cardiac output and arterial pressure. However, only the hyperosmotic/hyperoncotic solution effected a full restoration of baseline levels and resulted in sustained, near normal functioning. No other solution produced so full or sustained a response. The animals exhibited no apparent ill effect from the experimental protocol.

EXAMPLE II

PHYSIOLOGICAL MEASUREMENTS

Vascular pressures were measured with a Gould P23 pressure transducer (Gould, Incl, Oxnard, Calif.) connected to a multichannel strip chart recorder for continuous monitoring. Transducers were leveled to the point of the shoulder. Cardiac output was measured by thermodilution, using a Model 9520A Cardiac Output Computer (Edwards Laboratories, Santa Ana, Calif.). Urine was collected in a closed drainage system equipped with a graduated cylinder. Hematocrits were determined with an IEC Microhematocrit Centrifuge (Damon Instruments, Needham Heights, Mass.). Sodium and potassium were measured by a Model 143 Flame Photometer (Instrumentation Laboratories, Lexington, Mass.). Blood urea nitrogen and creatinine were measured on a Clinical Chemical Analyzer System 103 (Gilford Instruments, Oberlin, Ohio). Osmolarity was determined on an Osmette A Freeze Point Osmometer (Precision Instruments, Sudbury, Mass.). Plasma volume was measured by the Evans Blue dye dilution technique (Gibson et al., J. Clin. Invest., 16:301 (1937) which is incorporated by reference).

EXAMPLE III

COMPARATIVE EFFICACY OF SOLUTIONS TESTED

Studies were performed to compare the efficacy of a hyperosmotic/hyperoncotic solution (1.2M NaCl, 6% dextran 70), with a hyperosmotic sodium chloride solution (1.2M), a hyperoncotic dextran solution (6%) and with no resuscitative measures.

FIGS. 1 and 2 depict the effect which these solutions have on arterial pressure and cardiac output, respectively. Baseline arterial pressure ranged from about 86 to 101 mm Hg. In order to induce hypodynamic circulatory shock, the pressure was reduced to about 50 mm Hg. When no resuscitative measures were undertaken, this level rose spontaneously to about 65 mm Hg. An infusion of a small volume of dextran solution resulted in elevation of arterial pressure to about 70 mm Hg, but this level deteriorated over the course of the following three hours. An infusion of either the hyperosmotic sodium chloride solution or the hyperosmotic sodium chloride/hyperoncotic dextran solution resulted in an immediate return to baseline levels. With the hyperosmotic sodium chloride solution, however, the arterial pressure declined some 20% below baseline. The hyperosmotic sodium chloride/hyperoncotic dextran solution effects a rapid, immediate, sustained return of arterial pressure to baseline levels.

Cardiac output decreased from about 5 l/min to about 2.25 l/min upon bleeding. An infusion of a small amount of hyperoncotic dextran solution resulted in a small improvement in cardiac output while an infusion of hyperosmotic sodium chloride solution resulted in a transient return to baseline, followed by rapid deterioration. Infusion of the hyperosmotic sodium chloride/hyperoncotic dextran solution, however, not only immediately resulted in cardiac output even somewhat above baseline but a sustained level at or near baseline as well. Thus, the hyperosmotic/hyperoncotic solution results in a rapid and sustained normalization of cardiac output.

Different hyperoncotic colloid solutions were also compared. In addition to the studies referred to above utilizing hyperoncotic dextran 70, experiments were performed utilizing 1.2M sodium chloride solutions to which different colloids were added in hyperoncotic concentrations. These included hyperoncotic human albumin (25% weight/volume), hyperoncotic dextran 40 (15% weight/volume) and hyperoncotic hydroxyethyl starch (6% weight/volume). The oncotic pressure of these solutions is not known precisely, but such is well above 70 mm Hg and presumably above 150 mm Hg. Two hundred milliliters of each solution were used in an experimental protocol as in Example I. Results of the cardiac output responses are shown in Table I.

TABLE I

DIFFERENT HYPERONCOTIC SOLUTIONS EACH MIXED WITH 1.2 M SODIUM CHLORIDE IN DEIONIZED STERILE WATER
Cardiac Output (liters/minute)

|  | 25% Albumin | 15% Dextran 40 | 6% Starch |
|---|---|---|---|
| Baseline | 4.3 | 5.2 | 5.6 |
| Hemorrhage | 1.75 | 2.3 | 2.9 |
| 10 min. post resuscitation | 8.5 | 5.3 | 5.6 |
| 60 min. post resuscitation | 6.9 | 5.6 | 6.5 |
| 120 min. post resuscitation | 6.9 | 5.0 | 6.4 |

All hyperosmotic/hyperoncotic solutions resulted in an immediate and sustained improvement in cardiovascular function.

Different hyperosmotic sodium chloride solutions (1200, 1800, 2400 and 3600 mOsms) and an isoosmotic sodium chloride solution (about 285 mOsms), each mixed with 6% dextran 70 (70 mm Hg) were also compared. Results of these studies are shown in Table II. All hyperosmotic solutions were more effective than the isoosmotic solution. Cardiovascular response generally improved as osmolarity increased to 2400 mOsms. Concentrations equivalent to 3600 mOsms and higher caused convulsions. Data suggests 2400 mOsms sodium chloride/70 mm Hg dextran solution is near optimal.

TABLE II

SODIUM CHLORIDE SOLUTIONS OF DIFFERENT OSMOLARITIES, EACH MIXED WITH 6% DEXTRAN 70
Cardiac Output (liters/minute)

|  | 300 | 1200 | 1800 | 2400 | Osmolarity 3600 |
|---|---|---|---|---|---|
| Baseline | 5.1 | 5.9 | 4.9 | 5.3 | 4.3 |
| Hemorrhage | 2.2 | 2.3 | 2.1 | 2.2 | 1.8 |
| 10 min. post resuscitation | 3.2 | 4.6 | 5.0 | 6.2 | 7.0* |
| 60 min. post resuscitation | 3.1 | 4.3 | 4.8 | 4.9 | 4.8 |
| 120 min. post resuscitation | 3.2 | 4.4 | 4.3 | 4.7 | 4.3 |

*Convulsion occured after infusion with 3600 mOsm solution.

The efficacy of a total of 6 solutions having osmolarities of about 2400 mOsms, but varying in ionic compositions and concentrations were compared using the experimental protocol in Example I. All solutions were made up in sterilized deionized water and included aqueous solutions of sodium chloride, sodium chloride/sodium acetate, sodium chloride/mannitol, sodium chloride/dextran, glucose and sodium bicarbonate, starch, dextran, and albumin. The solutions tested are listed in Table III.

TABLE III

SIX 2400 mOsms SOLUTIONS

| | |
|---|---|
| NaCl | 1.2 M NaCl |
| NaHCO$_3$ | 1.2 M NaHCO$_3$ |
| NaAc | 0.6 M NaCl and 0.6 M NaAcetate |
| Man | 0.7 M NaCl and 1.0 M Mannitol |
| Dex | 1.2 M NaCl and 6% Dextran 70 |
| Glu | 2.4 M Glucose |

The results of the tests with these various solutions are presented in Table IV. All hyperosmotic crystalloid solutions caused a rapid improvement in cardiac output. However, the response was only sustained with the addition of a hyperoncotic colloid. With a hyperosmotic/hyperoncotic solution, such as sodium chloride (2400 mOsms)/dextran 70 (70 mm Hg), the sheep exhibited a sustained normalization of cardiac output, oxygen consumption, vascular pressures, urine output and total peripheral resistance.

TABLE IV

SIX 2400 mOsms SOLUTIONS
EFFECTS ON CARDIAC OUTPUT (liters/minute)

| | NaCl | NaHCO$_3$ | NaAc | Man | Dex | Glu |
|---|---|---|---|---|---|---|
| Baseline | 5.1 | 5.3 | 5.5 | 5.0 | 5.3 | 5.3 |
| Hemorrhage | 2.3 | 2.0 | 2.3 | 2.1 | 2.2 | 2.1 |
| 10 min. post resuscitation | 5.3 | 4.0 | 6.3 | 5.0 | 6.2 | 5.3 |
| 60 min. post resuscitation | 3.9 | 3.5 | 3.9 | 3.4 | 4.9 | 3.3 |
| 120 min. post resuscitation | 3.6 | 3.0 | 3.5 | 3.2 | 4.7 | 3.2 |
| 180 min. post resuscitation | 3.8 | — | 3.9 | — | 5.0 | — |

EXAMPLE IV

SURVIVORSHIP OF ANIMALS TREATED WITH VARIOUS FLUIDS

Experimental tests performed by Dr. Peter Maningas at the U.S. Army's Letterman Institute of Research have confirmed the efficacy of hyperosmotic/hyperoncotic solutions for treating hypodynamic shock. Experiments compared the effects of hyperosmotic and hyperoncotic solutions on survival in a severe hemorrhage rapid exsanquination model in swine (Traverso, Circulatory Shock, 12:1, (1984) which is incorporated by reference). Adult swine which were bled to 50 of estimated blood volume in 15 minutes, were treated with small resuscitation volumes of the following aqueous solutions: isoosmotic sodium chloride solution; hyperosmotic sodium chloride solution (2400 mOsms); hyperoncotic dextran solution (70 mm Hg); and hyperosmotic sodium chloride (2400 mOsms)/hyperoncotic dextran (70 mm Hg) solution. Survival rates are shown in Table V. There was 100% survival with a solution of hyperosmotic/hyperoncotic solution while only limited success was achieved with solutions of either solute alone. No animals survived with isotonic saline or with no treatment.

TABLE V

SWINE SURVIVAL AFTER RAPID 50% BLOOD LOSS

| Resuscitation Fluid | Survival |
|---|---|
| Isoosmotic Sodium Chloride | -0- |
| Hyperosmotic Sodium Chloride | 50% |
| Hyperoncotic Dextran | 66% |
| Hyperosmotic Sodium Chloride/ Hyperoncotic Dextran Solution | 100% |

EXAMPLE V

USE OF HYPEROSMOTIC/HYPERONCOTIC SOLUTION TO TREAT HYPODYNAMIC SHOCK

A paramedic gives about 200–300 ml of a hyperosmotic/hyperoncotic solution by bolus injection into the peripheral vein of a trauma victim experiencing shock or threatening to experience shock at the scene of an accident. This small volume rapidly stabilizes the patient's circulatory function until arrival at an emergency room or trauma center. This rapid restoration of cardiac output, blood pressure, renal function and oxygen consumption lowers the morbidity and mortality of trauma and hemorrhage.

Small volume resuscitation is also effective in several other hypodynamic circulatory states, such as during and after extensive surgical procedures, for burn injury and after organ transplantation, where hypodynamic shock is threatened or experienced.

Although the invention has been described with reference to the presently-preferred embodiment, it should be understood that various modifications can be made by those skilled in the art without departing from the invention. Accordingly, the invention is limited only by the following claims.

We claim:

1. A physiologically acceptable solution for treating hypodynamic circulatory shock in a mammal, said solution containing a crystalloid having a molecular weight less than about 1000 in a concentration of at least about 1800 mOsms and a colloid having a molecular weight in excess of 30,000 in a concentration so as to render said solution hyperoncotic relative to the colloidal osmotic pressure of the normal blood plasma of said mammal.

2. The physiologically acceptable solution of claim 1, wherein the crystalloid is selected from the group consisting of physiologically acceptable sodium salts, sugar alcohols, and sugars.

3. The physiologically acceptable solution of claim 1, wherein said crystalloid concentration is in excess of about 1800 mOsms.

4. The physiologically acceptable solution of claim 1, wherein said crystalloid concentration is about 2400 mOsms.

5. The physiologically acceptable solution of claim 1, wherein said colloid is selected from the group consisting of physiologically acceptable dextran, hydroxyethyl starch, or protein.

6. The physiologically acceptable solution of claim 1, wherein said hyperoncotic concentration is at least about 70 mm Hg.

7. A physiologically acceptable solution comprising saline and dextran, having an osmolarity of about 2400 mOsms and an oncocity of about 70 mm Hg.

8. A method of preventing or treating hypodynamic circulatory shock in a mammal, comprising the step of administering to said mammal in a condition of existing or impending shock, a therapeutically effective dose of a physiologically acceptable solution, said solution containing a crystalloid having a molecular weight less than about 1000 in a concentration of at least about 1800 mOsms and a colloid having a molecular weight in excess of 30,000 in a concentration so as to render said solution hyperoncotic relative to the colloidal osmotic pressure of the normal blood plasma of said mammal.

9. The method of claim 8, wherein said crystalloid is selected from the group consisting of physiologically acceptable sodium salts, sugar alcohols, and sugars.

10. The method of claim 8, wherein said crystalloid concentration is in excess of about 1800 mOsms.

11. The method of claim 8, wherein said crystalloid concentration is about 2400 mOsms.

12. The method of claim 8, wherein said colloid is selected from the group consisting of physiologically acceptable dextran, hydroxyethyl starch, and protein.

13. The method of claim 8, wherein said hyperoncotic concentration is in excess of about 30 mm Hg.

14. The method of claim 8, wherein said hyperoncotic concentration is at least about 70 mm Hg.

15. The method of claim 8, wherein said physiologically acceptable solution is infused intravascularly.

16. The method of claim 8, wherein said physiologically acceptable solution is injected.

17. The method of claim 8, wherein said therapeutically effective dose is about 4 to 5 ml/kg of body weight.

18. The physiologically acceptable solution of claim 1, wherein said hyperoncotic pressure is at least about 20 mm Hg.

19. The physiologically acceptable solution of claim 1 wherein said colloid is gelatin.

20. The method of claim 8 wherein said colloid is gelatin.

* * * * *

UNITED STATES PATENT AND TRADEMARK OFFICE
CERTIFICATE OF CORRECTION

PATENT NO. : 4,908,350

DATED : March 13, 1990

INVENTOR(S) : KRAMER ET AL.

It is certified that error appears in the above-identified patent and that said Letters Patent is hereby corrected as shown below:

In column 1, line 32, delete "n" and insert therefor --on--.

In column 7, line 55, after 50 insert --%--.

In column 10, line 14, delete "20" and insert therefor --30--.

Signed and Sealed this

Nineteenth Day of November, 1991

Attest:

HARRY F. MANBECK, JR.

*Attesting Officer*     *Commissioner of Patents and Trademarks*